(12) United States Patent
Hollawell

(10) Patent No.: US 8,486,069 B2
(45) Date of Patent: Jul. 16, 2013

(54) EXTERNAL FIXATOR

(75) Inventor: Shane M. Hollawell, Wall, NJ (US)

(73) Assignee: Wright Medical Technology, Inc., Arlington, TN (US)

(*) Notice: Subject to any disclaimer, the term of this patent is extended or adjusted under 35 U.S.C. 154(b) by 0 days.

(21) Appl. No.: 13/551,185

(22) Filed: Jul. 17, 2012

(65) Prior Publication Data
US 2012/0283736 A1  Nov. 8, 2012

Related U.S. Application Data

(63) Continuation of application No. 12/643,371, filed on Dec. 21, 2009, now Pat. No. 8,235,994, which is a continuation of application No. 11/368,783, filed on Mar. 6, 2006, now abandoned.

(60) Provisional application No. 60/659,227, filed on Mar. 7, 2005.

(51) Int. Cl.
*A61B 17/00* (2006.01)
*A61F 4/00* (2006.01)
*A61F 5/04* (2006.01)

(52) U.S. Cl.
USPC .................................................. 606/59

(58) Field of Classification Search
USPC ....................................... 606/53–59
See application file for complete search history.

(56) References Cited

U.S. PATENT DOCUMENTS

| | | |
|---|---|---|
| 4,365,624 A | 12/1982 | Jaquet |
| 4,393,868 A | 7/1983 | Teague |
| 4,604,997 A | 8/1986 | De Bastiani et al. |
| 4,611,586 A | 9/1986 | Agee et al. |
| 4,620,533 A | 11/1986 | Mears |
| 4,628,919 A | 12/1986 | Clyburn |
| 4,895,141 A | 1/1990 | Koeneman et al. |
| 4,920,959 A | 5/1990 | Witzel et al. |
| 4,922,896 A | 5/1990 | Agee et al. |
| 4,978,347 A | 12/1990 | Ilizarov et al. |
| 5,067,954 A | 11/1991 | Ilizarov |
| 5,108,394 A | 4/1992 | Kurokawa et al. |
| 5,320,622 A | 6/1994 | Faccioli et al. |
| 5,397,322 A | 3/1995 | Campopiano |
| 5,437,667 A | 8/1995 | Papierski et al. |
| 5,527,309 A | 6/1996 | Shelton |
| 5,571,103 A | 11/1996 | Bailey |
| 5,591,169 A | 1/1997 | Benoist |
| 5,658,283 A | 8/1997 | Huebner |
| 5,662,649 A | 9/1997 | Huebner |
| 5,683,389 A | 11/1997 | Orsak |
| 5,741,251 A | 4/1998 | Benoist |

(Continued)

FOREIGN PATENT DOCUMENTS

| | | |
|---|---|---|
| WO | 8503449 | 8/1985 |
| WO | 9812975 | 4/1998 |

OTHER PUBLICATIONS

Gradl, et al., "Fractures of the Distal Radius Treated With a Nonbridging External Fixation Technique Using Multiplanar K-Wires", The Journal of Hand Surgery, 2005, 30A:960-968.

*Primary Examiner* — Sameh Boles

(74) *Attorney, Agent, or Firm* — Duane Morris LLP

(57) ABSTRACT

A fixator for use in the reconstruction of acute, chronic and traumatic injuries to the upper and lower extremities. The fixator has a unique clamping system that allows for the snapping in of pins and rails, and for multi-planar fixation of bones.

11 Claims, 4 Drawing Sheets

U.S. PATENT DOCUMENTS

| | | | |
|---|---|---|---|
| 5,743,898 A | 4/1998 | Bailey et al. |
| 5,752,954 A | 5/1998 | Mata et al. |
| 5,810,814 A | 9/1998 | Newson |
| 5,891,144 A | 4/1999 | Mata et al. |
| 5,941,879 A | 8/1999 | Walulik et al. |
| 6,001,097 A | 12/1999 | Campopiano et al. |
| 6,053,915 A | 4/2000 | Bruchmann |
| 6,283,964 B1 | 9/2001 | Weiner |
| 6,328,737 B1 | 12/2001 | Moorcroft et al. |
| 6,428,540 B1 | 8/2002 | Claes et al. |
| 6,527,775 B1 | 3/2003 | Warburton |
| 6,629,976 B1 | 10/2003 | Gnos et al. |
| 6,716,212 B1 | 4/2004 | Pickens |
| 6,793,655 B2 | 9/2004 | Orsak |
| 6,866,665 B2 | 3/2005 | Orbay |
| 2003/0109879 A1 | 6/2003 | Orsak |
| 2004/0133200 A1 | 7/2004 | Ruch et al. |
| 2005/0043730 A1 | 2/2005 | Janowski et al. |

US 8,486,069 B2

EXTERNAL FIXATOR

CROSS-REFERENCE TO RELATED APPLICATIONS

This application is a continuation application of U.S. application Ser. No. 12/643,371, filed on Dec. 21, 2009, which claims priority from Ser. No. 11/368,783, filed on Mar. 6, 2006, which claims priority from U.S. Provisional Patent Application No. 60/659,227, filed on Mar. 7, 2005, the entireties of which are incorporated by reference herein.

FIELD OF THE INVENTION

The present invention relates generally to external fixation devices, and more particularly to an external fixation device for use in the reconstruction of acute, chronic and traumatic injuries to the upper and lower extremities.

BACKGROUND OF THE INVENTION

In the medical field, patients can suffer from acute, chronic, and/or traumatic injuries to the upper and lower extremities. In such circumstances, it is often desirable to stabilize and reconstruct the bones of the afflicted area. To that end, systems have been developed to help stabilize and reconstruct injured bones. One type of system employed in the past is an external fixation system.

All bone injuries are not the same. As a result, the best mode of treatment for a bone injury can vary significantly depending on the size of the person, size of the injured bone, and type of bone injury. Specifically, it is often times desirable to have an external fixation device that is capable of accommodating a wide variety of pin placements. However, it is simultaneously desirable to have a relatively simple system that can be readily taught to practitioners in the field. Further, it is also necessary to have a stable system that effectively treats the bone injury. Finally, it is desirable to have a cost effective system. It is therefore desirable to have an external fixation device that allows for versatile pin placement, is relatively simple, stable, and cost effective.

SUMMARY OF THE INVENTION

The present invention comprises an external fixation device ("fixator") for use in the reconstruction of acute, chronic and traumatic injuries to the upper and lower extremities. The fixator's functions include, but are not limited to, immobilization, compression, joint realignment, arthrodesis, bone distraction and lengthening, fracture reduction/stabilization, and treatment of Charcot arthropathy. More specifically, potential uses for the fixator include acute stabilization and chronic reconstruction of bones, particularly those of the hand or foot. Advantages of using the fixator include, but are not limited to, the ability to gradually correct over time, to fixate away from the injury site if necessary, to provide additional manipulation or additional correction, and to provide assistance in interpositional bone grafting.

The fixator can be used in multi-planar and multi joint correction, is percutaneous and, therefore, minimally invasive, and can provide additional stability and mobility when compared to fixation devices currently in use. Additional advantages of the present invention over existing devices include the design and adjustability to easily assemble and disassemble components of the system without disturbing pins already set into the patient's bone or the rest of the system itself.

BRIEF DESCRIPTION OF THE DRAWINGS

The features of the present invention which are believed to be novel are set forth with particularity in the appended claims. The drawings may not be to scale. The invention may best be understood by reference to the following description taken in conjunction with the accompanying drawings, in the several figures of which like reference numerals identify like elements, and in which:

DETAILED DESCRIPTION OF THE INVENTION

Figure 1:
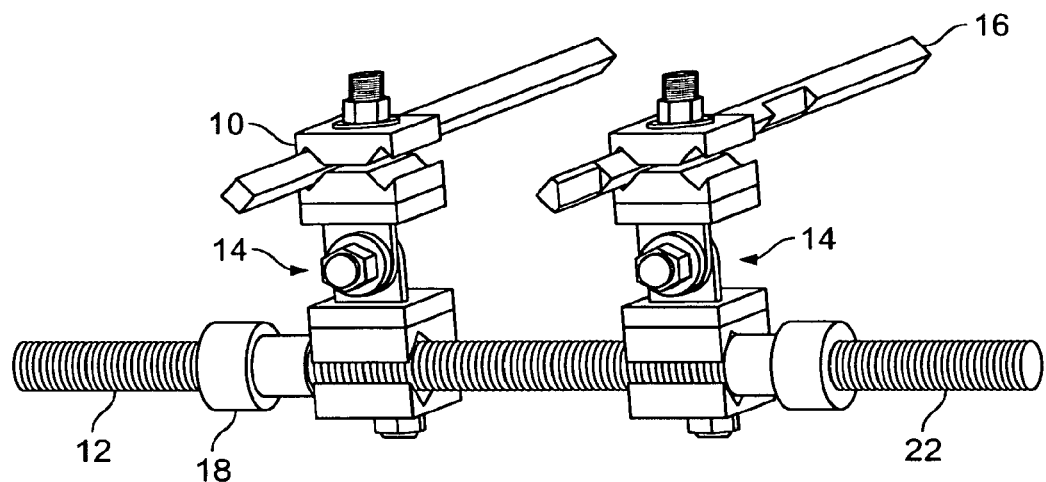
FIG. 1 is a side perspective view of one embodiment of the fixator.
Figure 2:
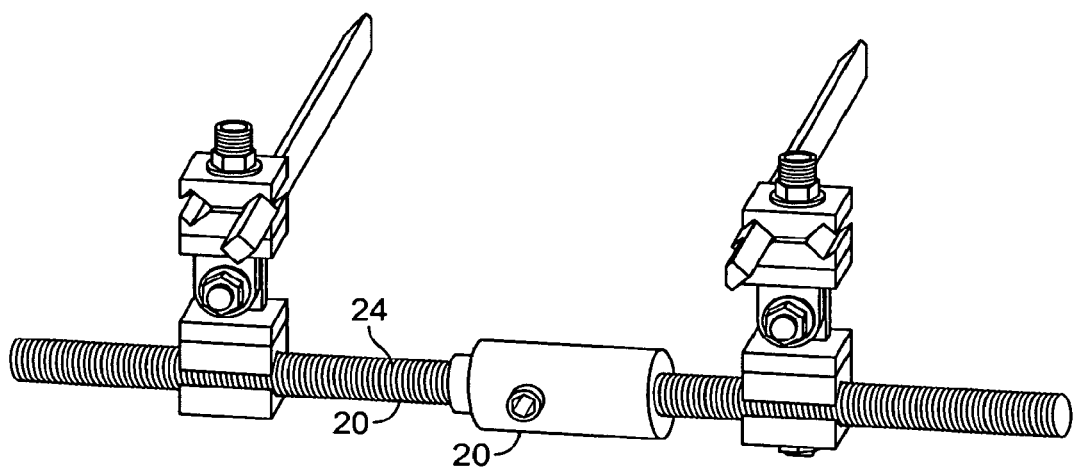
FIG. 2 is a side perspective view of a second embodiment of the fixator.

While the present invention is susceptible of embodiments of various forms, there is shown in the drawings, and will hereinafter be described some exemplary and non-limiting embodiments, with the understanding that the present disclosure is to be considered an exemplification of the invention. It is not intended to limit the invention to the specific embodiments listed.

As can be seen in FIGS. 1-7, in one embodiment of the present invention, a fixator 10 comprises a rail 12, at least one clamp system 14, and a pin 16. Generally, the clamp system 14 is configured to attach to both the rail 12 and the pin 16, which is connected to the bone 40 for fixation and stabilization. The fixator 10 may further include compression and distraction nuts 18 functionally connected to the fixator 10 to allow for additional manipulation of bone healing and growth. The clamp systems 14 can be splined to receive and hold rails 12 and pins 16.

The rails 12 may be any size or shape, and persons of skill in the art will recognize that different application require rails 12 of many differing sizes or shapes, all of which are contemplated herein. The rails 12 may, for example, have a circular, oblong, square, rectangular, or other-shaped cross section. Typically, however, the rails 12 have a round or circular cross-section and are sized in a manner suitable for fixation of small bones 41, such as those of the foot or hand. The rails 12 may be composed of many materials including, for example, carbon fiber or high density plastic, which allows the rod to be radiolucent. Optionally, the rails 12 may also be threaded to allow for attachment of clamp systems 14, distraction/compression nuts 18, or other components of a fixator 10.

In one embodiment of the present invention, the rail 12 has a "negative" thread pattern, in which the threads 22 are grooves in the surface of the rail 12 rather than protrusions. In this specification, reference to a threaded component will be a disclosure of both a positive and negative thread. The negative thread pattern allows, for example, the clamp system 14 to easily slide up and down the rail 12, while still allowing for the attachment of compression nuts 18 or other components which could be threaded onto the rail 12. In such situations, the corresponding component, such as a compression nut 18, will have a positive thread pattern. In a preferred embodiment, the rail 12 has a thread pitch of approx 1 mm so one revolution of around the threaded rail 12 produces 1 mm of linear movement. In another embodiment, the rail 12 can be geared. In such an embodiment, the rail has a rack and pinion design 20 that allows for compression or distraction. This geared version can have a scale 24 indicating the amount of compression or distraction.

Figure 6:
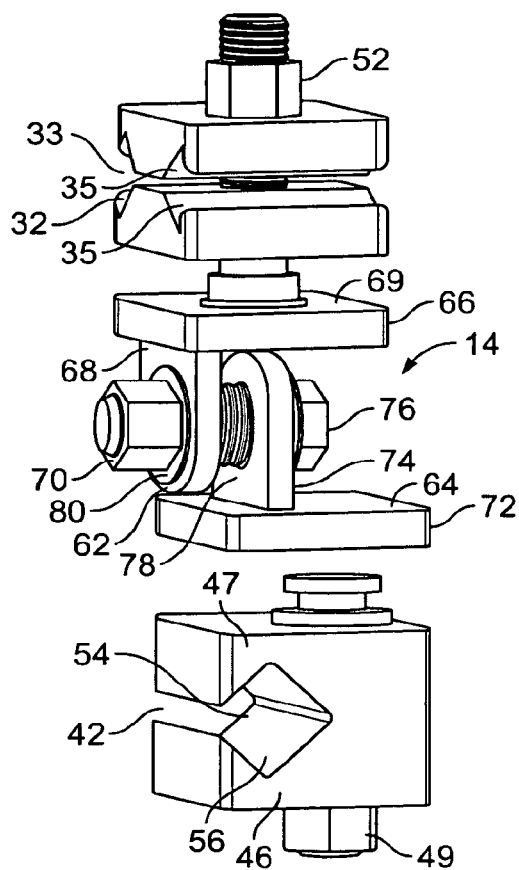
FIG. 6 is an angled view of one embodiment of parts of the clamp system.
Figure 7:
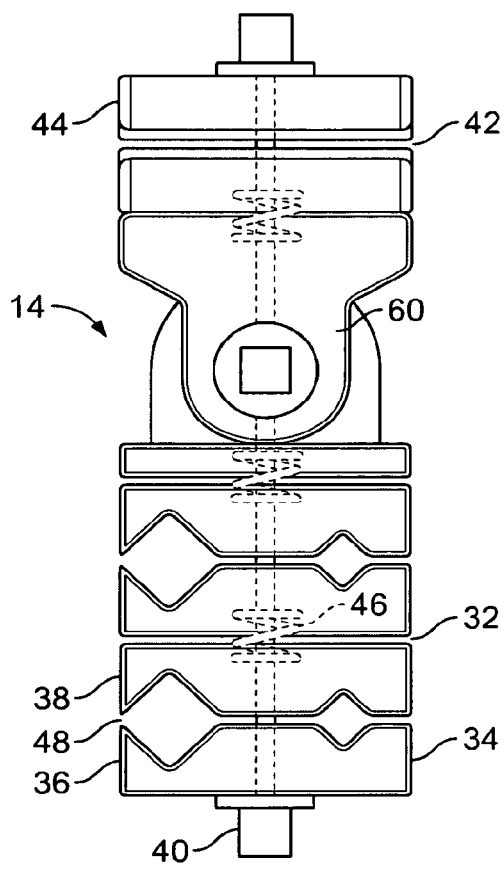
FIG. 7 is a side view of one embodiment of the clamp system.

As can be seen more specifically in FIGS. 6 and 7, in a preferred embodiment, the clamp system 14 comprises a first clamp area 32 and a second clamp area 42. Preferably, the first clamp area 32 comprises a pin clamp 34 while the second clamp area 42 comprises a rail or bar clamp 44. Preferably, the first clamp area 32 is functionally connected to the second clamp area 42 such that the object held by the different clamp areas, either pins 16 or rails 12, can lie in different planes.

Preferably, the first clamp area 32 is a pin clamp 34 that can comprise a pin clamp top 36, a pin clamp bottom 38 and a first clamp bolt 40. The pin clamp top 36 and bottom 38 are each configured to allow the first clamp bolt 40 to pass through them. In one embodiment, the first clamp bolt 40 is threaded, and the pin clamp top 36 and pin clamp bottom 38 have internal, threaded holes configured to receive the threaded first clamp bolt 40. When held by the first clamp bolt 40, the pin clamp top 36 and bottom 38 can be thought of as a set that together define at least one pin passage 33 capable of receiving the pin 16. Preferably, the pin clamp top and bottom 36, 38 each have inner surfaces 35 that together define two distinct pin passages 33 each capable of receiving the pin 16. It is preferred that the inner surfaces 35 of the pin passages 33 be textured to allow for more secure engagement of the pin 16. For example, the inner surfaces 35 may have a 2× diamond face with grooves 90 degrees to each other. In addition to the inner surfaces 35 being textured, other surfaces of the pin clamp top and bottom 36, 38 may be textured where a more secure engagement is desired.

In one embodiment, the two distinct pin passages 33 are configured to receive the same size pin 16. In another embodiment, one pin passage 33 is configured to receive one size pin 16, for example a half pin, while the other pin passage 33 is configured to receive a second size pin 16, for example a transfixing pin. It is contemplated that the pin passage 33 will extend in a direction substantially perpendicular to the first clamp bolt 40. In one embodiment, the pin clamp top and bottom 36, 38 can be rotated around the first clamp bolt 40 such that the pins 16 can be orientated in any direction in the plane perpendicular to the first clamp bolt 40.

In a preferred embodiment, the first clamp area 32 further comprises another pin clamp 34 or a rail clamp 44. An example of a first clamp area 32 with at least two pin clamps can be found in FIG. 7. As can be seen in FIG. 7, two sets of pin clamp top and bottom clamps 36, 38 can be arranged proximate each other on the pin clamp bolt 40. In such a set up, four distinct pin passages 33, each capable of receiving a pin 16, can be defined by the pin clamp top and bottoms 36, 38. In a preferred embodiment, the first clamp area 32 further comprises springs 46 which are functionally attached to the first clamp area 32 and that exert pressure on some of the pin clamp tops and bottoms 36, 38. In such a configuration, the pin clamps 34 can be "snap in." That is, one can exert force on the pin clamp top and/or bottom 36, 38. When so doing, the pin clamp top and/or bottom 36, 38 will push against the springs 46 and thereby be in a position that defines an opening 48 leading into the pin passage 33 capable of allowing the pin 16 to be pressed into that pin passage 33. When the force is released, the springs 46 again exert full pressure on the pin clamp top and/or bottom 36, 38, causing the pin clamp top and bottom 36, 38 set to clamp on the pin 16 and hold it in a fixed position. In addition, a nut 52 can then be tightened to more securely hold the rail 12 or pin 16 in place.

Figure 5:
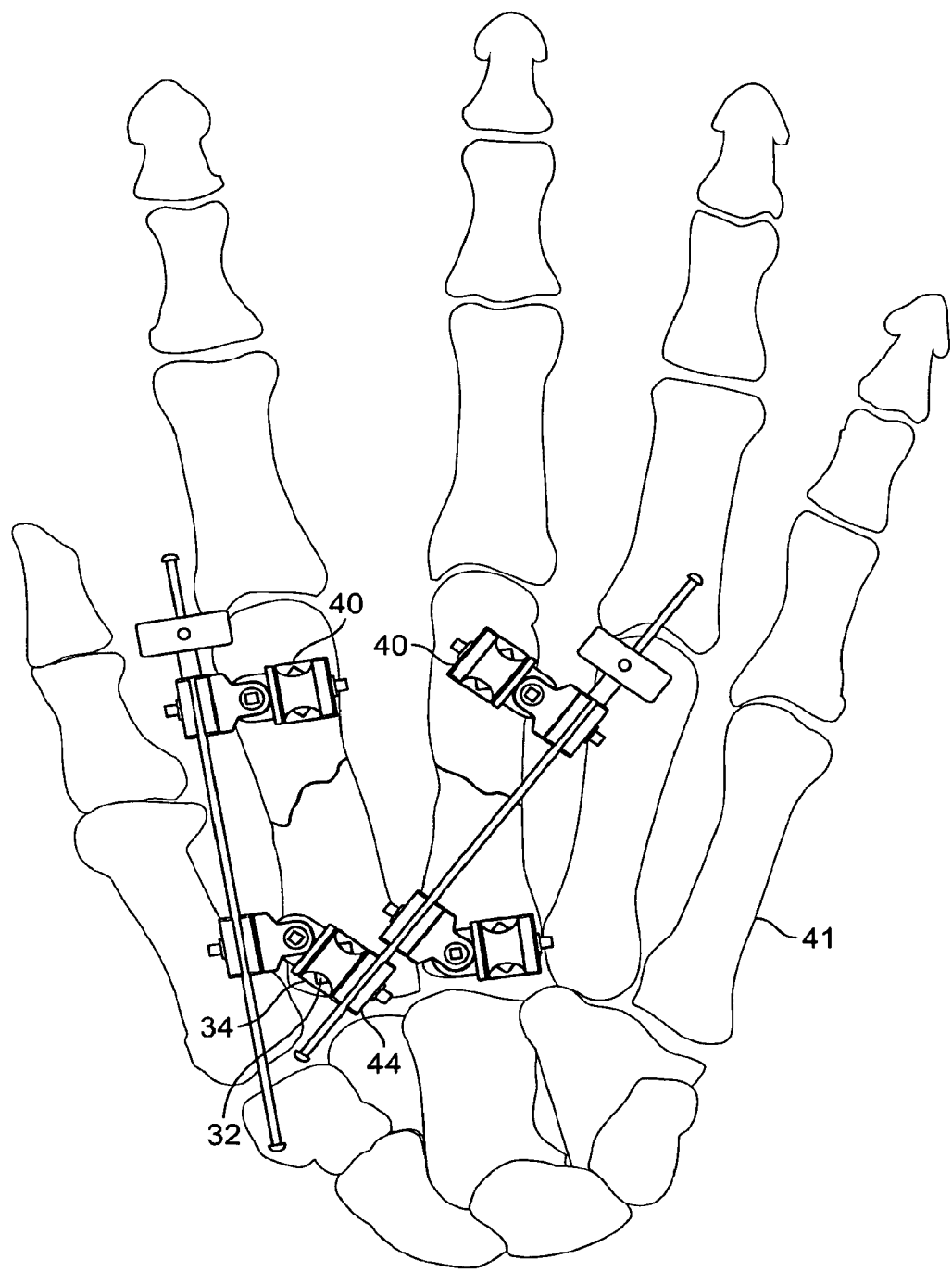
FIG. 5 is a top view of one embodiment of the fixator.

In another embodiment, the first clamp area further comprises a rail clamp 44. The rail clamp 44 comprises a rail clamp top 46, a rail clamp bottom 47 and a rail clamp bolt 49. The rail clamp top and bottom 46, 47 are each configured to allow the rail clamp bolt 49 to pass through them. In one embodiment, the rail clamp bolt 49 is threaded, and the rail clamp top and rail clamp bottom 46, 47 have internal, threaded holes configured to receive the threaded rail clamp bolt 49. When held by the rail clamp bolt 49, the rail clamp top and bottom 46, 47 can be thought of as a set that together define at least one rail passage 54 capable of receiving the rail 12. It is contemplated that the inner surfaces 56 of the rail passage 54 can be textured to allow for more secure engagement of the rail 12. For example, the inner surfaces 56 may have a 2.times. diamond face with grooves 90 degrees to each other. In addition to the inner surfaces 56 being textured, other surfaces of the rail clamp top and bottom 46, 47 may be textured where a more secure engagement is desired. As seen in FIG. 5, the first clamp area 32 can comprise a rail clamp 44 and a pin clamp 34. In such cases, the rail passage 54 can be in a different plane than the pin passage 33. The first clamp area 32 can be configured to allow for the rail 12 in the rail passage 54 to be disposed in a different direction than the pin 16 in the pin passage 33. For example, the pin 16 may extend at an angle generally perpendicular to the bone or bones 41 to be fixed so that it can be anchored in the bone 41 while the rail 12 may extend at an angle generally parallel to the bone or bones 41 to be fixed.

In one embodiment, a hinge 60 is attached to the first clamp bolt 40 proximate to either a pin or rail clamp bottom 38, 47. In a preferred embodiment, the hinge 60 has a male element 62 and a female element 64. The use of the terms male and female elements 62, 64 is not meant to suggest a certain structure, but only to disclose that the two elements are configured to work together to provide a hinged connection. The male element 62 has a first section 66 and a second section 68 that are connected to each other. The first section and the second section 66, 68 can be disposed at about a 90 degree angle in relation to each other. Preferably, the first section 66 is configured to receive the first clamp bolt 40 by having a hole therethrough. The hole may be threaded. It is also preferred that the surface 69 of the first section 66 proximate the pin clamp 34 be textured. For example, the surface may have a 2× diamond face with grooves 90 degrees to each other. Preferably, the second section 28 is configured to receive a hinge bolt 70 by having a hole therethrough. The hole may be threaded.

The female element 64 can have a first section 72 that is connected to a second section 74, preferably at about a 90 degree angle in relation to each other. The first section 72 of the female element 64 is preferably configured to receive a rail clamp bolt 49 by having a hole therethrough. The second section 74 of the female element 64 can have a hole therethrough that is able to accommodate the hinge bolt 70. The female element 64 is hingedly connected to the male element 62. In a preferred embodiment, both the female element 64 and the male element 62 are disposed on the hinge bolt 70, and are held thereon by a hinge retaining washer or nut 76. When the hinge bolt 70 and retaining washer or not 76 are loose, the female element 64 can be rotated in relation to the male element 62, and vice versa. To stabilize the connection, the hinge bolt 70 is tightened, thus holding the male element 62 against the female element 64. The surfaces 78 of the female and male elements 62, 64 that come into contact with each other may be textured to increase friction and create a more stable connection. In addition, washers 80 may be employed to ensure a stable connection.

In a preferred embodiment, the first clamp area 32 is connected via the hinge 60 to the second clamp area 42. The second clamp area 42 can comprise a pin clamp 34, a rail clamp 44, or a combination of pin and rail clamps, 32, 44. Preferably, each clamp system 14 allows for multi-planar attachment of rails 12 and pins 16.

Figure 3:
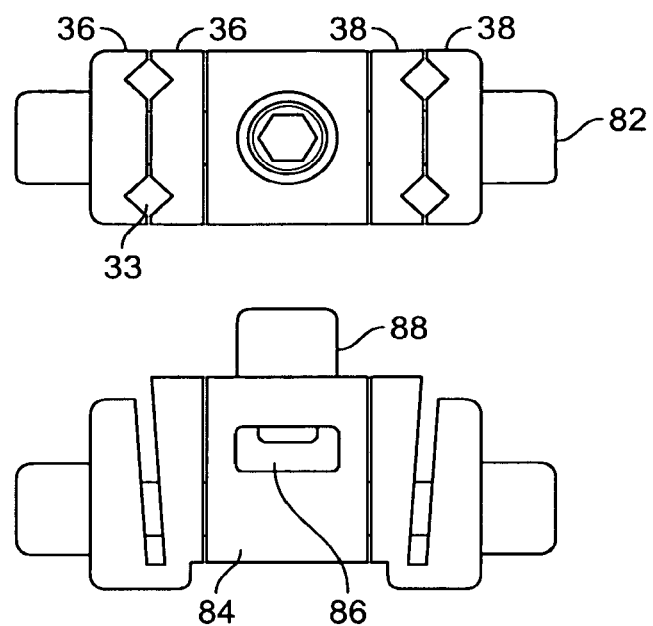
FIG. 3 is a side and top view of one embodiment of a clamp system.
Figure 4:
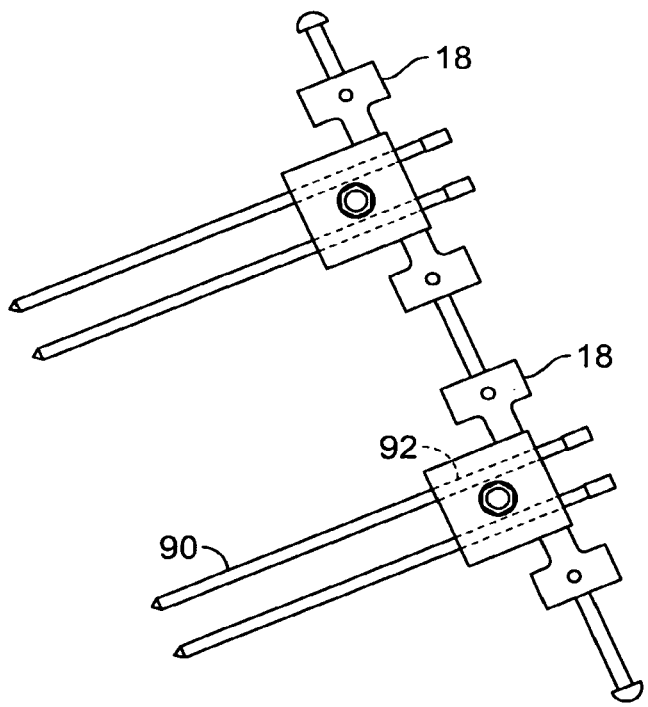
FIG. 4 is a side view of one embodiment of the fixator.

In another embodiment, the clamp system 14 comprises one clamp area. In such a system, the one or more pin clamps 32 and one or more rail clamps 34 can be linearly attached to the same bolt 82. For example, as can be seen in FIG. 3, such a clamp system comprises one or more pin clamp tops 36 held in spaced relation to one or more corresponding pin clamp bottoms 38. Together, the pin clamp top and bottom 36, 38 define a pin passage 33 that can accept a pin 16. The pin clamp tops and bottoms 36, 38 are configured with a hole therethrough that accepts a pin clamp bolt 82. The pin clamp tops and bottoms 36, 38 can be loosened and tightened to accept a pin 16 and then securely attach to that pin 16. This embodiment of a clamp system 14 further comprises a clamp body 84 that preferably is configured with a hole therethrough that can accept the pin clamp bolt 82. The clamp body 84 can further define a rail passage 86 that is capable of accepting a rail 12. The clamp body 84 can further comprises a device, such as a bar clamp bolt 88, that is capable of being screwed into the rail passage 86 to secure the rail 12.

The pins 16 can be half pins or transfixing pins. In practice, one part of the pin 90 is set into a patient's bones while a second part of the pin 92 is attached to a clamp area 32, 42. The configuration of the fixator 10 allows for such pins 16 to be placed prior to, during, or after assembly of the other parts of the fixator 10 without comprising the accuracy of the fixation.

As can be seen in FIGS. 1, 2, 4, and 5, it is contemplated that the fixator 10 comprise more than one clamp system 14. A first clamp system 14 is preferably attached to a bone 41 at a first location. A second clamp system 14 is preferably attached to a bone 41, either the same bone, or a different bone, at a second location. The two clamp systems 14 are connected by a rail 12, to which both clamps systems 14 are attached via the rail clamp 44. More than one clamp system 14 and more than one rail 12 can be utilized. In one embodiment, a first clamp system 14 has a rail clamp 44 attached to a first rail 12 and a pin clamp 34 attached to two pins 16. The pins 16 are attached to a bone 41 at a first location. A second clamp system 14 has a rail clamp 44 attached to the first rail 12, and a pin clamp 34 attached to two different pins 16, which are attached to a bone 41 at a second location. The second clamp system 14 also has a second rail clamp 44 attached to a second rail 12. A third clamp system 14 has a rail clamp 44 attached to the second rail 12 and a pin clamp 34 attached to two pins 16. These two pins 16 are attached to either the same bone 41, or a different bone. As can be seen, the fixator 10 described herein, with each clamp system 14 capable of being comprised of one or more adjustable rail or pin clamps 44, 34, allows for a wide range of fixator 10 configurations that allow for effective treatment of a number of injuries.

The clamps systems 14 are adjustable with respect to the rail 12 in that each clamp system 14 can slide up or down the rail 12 and also rotate around the rail 12 freely. Once the optimum position for each clamp system 14 is obtained, the clamp system 12 may then be fixed securely in place by simply tightening the rail clamp 44. Moreover, additional clamp systems 14 may be added to or removed from the fixator 10 easily, both prior to fixation and stabilization and at any point during the healing process, and any number of rail or pin clamps 44, 34 may be used, depending upon the number of rails or pins 12, 16 necessary for a given treatment.

The pins 16 can be placed independently of the fixator 10 because of the snap-in functionality of the clamp systems 14 and the ability of the fixator 10 to correct in all planes due to the multi-planar movement of the clamp systems 14.

In a further embodiment of the present invention, compression nuts and distraction nuts 18 can attached to the rails 12 and used in conjunction with the clamp systems 14 to further adjust bone healing and growth. The nuts 18 may be used to move the clamp systems 14 incrementally along the rail 12 without moving the pins 16 or other components of the fixator 10, thus providing additional correction on a minute scale during the healing or growth process. The compression nuts 18 are preferably attached on the rail 12 such that, when moved, they will force two clamp systems 14 to move closer to each other. The distraction nuts 18 are preferably attached on a rail 12 between two clamp systems 14 such that when the distraction nut 18 is moved, it will force one clamp system 14 away from the other. Preferably, more than one compression and or distraction nuts 18 can be attached to the same rail 12 to allow for compression or distraction, i.e., the movement of one or more than one clamp systems 14 in either direction along the rail 12. Optionally, the compression and distraction nuts 18 may have built in washers. Further, the compression and distraction nuts 18 may have a positive thread and can be used in conjunction with a round rail 12 having a negative thread, as described previously.

In a further embodiment of the present invention, the fixator 10 may be easily modified in many ways, such as for example to accommodate pins 16 of multiple diameters and lengths. Additionally, many various sizes and shapes of clamps systems 14, rails 12, and/or compression/distraction devices may be employed without detracting from the spirit of the invention. Clamp systems 14, pins 16, and rails 12 can be easily reproduced, for example, for medium and large applications as well, such as for use on long bones of the leg or arm.

Because of the exceptional adjustability of the fixator 10, the fixator described herein can be connected to various parts of the foot or other body parts without being limited by the configuration of the device. Further, the clamp systems 14 also have the mechanical ability to interconnect with other rails and fixation systems, allowing for multiple-rail systems or more complex applications.

In further embodiments of the present invention, for example, the fixator can be used in conjunction with foot plate ("U ring") attachments, wires, Ilizarov fixators, or any other compatible external fixator device (none of which are shown) through the use of pins, wires (not shown), and/or transfixing pins.

The fixator 10 can be comprised of a wide variety of materials. In a preferred embodiment, the components of the fixator 10 are composed of anodized aluminum, stainless steel, or composite polymer. Specifically, the pins 16 can be manufactured from 316L stainless steel and are preferably 2 mm, 2.5 mm, or 3 mm in length.

What is claimed is:
1. A clamp system for a fixator, comprising:
a hinge including
a first hinge element having first and second sections that are directly connected to one another such that the second section extends from a surface of the first section, the second section defining a first hole,
a second hinge element having third and fourth sections that are directly connected to one another such that the fourth section extends from a surface of the third section, the fourth section defining a second hole, and a hinge bolt configured to be received in the first and second holes for hingedly connecting the first and second hinge elements, the hinge bolt being completely surrounded by each of the first and second holes without contacting the first and third sections of the first and second hinge elements, respectively;

a first clamp including
- a first top defining a third hole,
- a first bottom defining a fourth hole, and
- a first clamp bolt configured to be received through the third and fourth holes so as to engage the first section of the first hinge element, but within a seventh hole defined by the first section of the first hinge element for clamping the first top and first bottom to the first element of the hinge, the first top and first bottom together defining a first passage when clamped together by the first clamp bolt when a spring is disposed between the first section of the first hinge element and the first bottom of the first clamp area; and a second clamp including
- a second top defining a fifth hole,
- a second bottom defining a sixth hole, and
- a second clamp bolt configured to be received through the fifth and sixth holes and within an eighth hole defined by the third section of the second hinge element so as to engage the third section of the second hinge element for clamping the second top and second bottom to the second hinge element of the hinge, the second top and second bottom together defining a second passage when clamped together by the second clamp bolt.

2. The clamp system of claim 1, further comprising a spring disposed between the third section of the second hinge element and the second bottom of the second clamp area.

3. The clamp system of claim 2, wherein the first passage is configured to receive a pin therein.

4. The clamp system of claim 1, wherein the second pass is configured to receive a rail therein.

5. A clamp system for a fixator, comprising:

a hinge including
- a first hinge element having first and second sections that are directly connected to one another such that the second section extends from a surface of the first section, the second section defining a first hole
- a second hinge element having a third and fourth sections that are directly connected to one another such that the fourth section extends from a surface of the third section, the fourth section defining a second hole, and
- a hinge bolt configured to be received in the first and second holes for hingedly connecting the first and second hinge elements, the hinge bolt being completely surrounded by each of the first and second holes without contacting the first and third sections of the first and second hinge elements, respectively;

a first clamp including
- a first top defining a third hole,
- a first bottom defining a fourth hole,
- a first clamp bolt configured to be received through the third and fourth holes so as to engage the first section of the first hinge element, but within a seventh hole defined by the first section of the first hinge element for clamping the first top and first bottom to the first hinge element, the first top and first bottom together defining a first passage when clamped together by the first clamp bolt;

a first spring disposed between the first hinge element and the first bottom of the first clamp; and a second clamp including
- a second top defining a fifth hole,
- a second bottom defining a sixth hole,
- a second clamp bolt configured to be received through the fifth and sixth holes and within an eighth hole defined by the third section of the second hinge element so as to engage the third section of the second hinge element for clamping the second top and second bottom to the second hinge element, the second top and second bottom together defining a second passage when clamped together by the second clamp bolt, wherein the clamp system further includes a second spring disposed between the second hinge element and the second bottom of the second clamp.

6. The clamp system of claim 5, wherein the first passage is configured to receive a pin therein.

7. The clamp system of claim 5, wherein the second pass is configured to receive a rail therein.

8. The clamp system of claim 7, wherein the first passage is configured to receive a pin therein.

9. The clamp system of claim 8, wherein the second pass is configured to receive a rail therein.

10. The clamp system of claim 9, wherein the first top and first bottom together define a plurality of parallel passages when clamped together by the first clamp bolt.

11. The clamp system of claim 10, wherein the second top and second bottom together define a plurality of parallel passages when clamped together by the second clamp bolt.

* * * * *